US012251571B2

(12) United States Patent
Wasserbauer et al.

(10) Patent No.: US 12,251,571 B2
(45) Date of Patent: Mar. 18, 2025

(54) LIGHT BASED THERAPY DEVICES AND METHODS

(71) Applicant: HAIR GROUP, LLC, Walnut Creek, CA (US)

(72) Inventors: Sara Wasserbauer, Walnut Creek, CA (US); Erik Carlson, Walnut Creek, CA (US); Craig Janik, Walnut Creek, CA (US); Steven Escobar, Walnut Creek, CA (US)

(73) Assignee: HAIR GROUP, LLC, Walnut Creek, CA (US)

( * ) Notice: Subject to any disclaimer, the term of this patent is extended or adjusted under 35 U.S.C. 154(b) by 364 days.

(21) Appl. No.: 17/697,913

(22) Filed: Mar. 17, 2022

(65) Prior Publication Data

US 2022/0203117 A1   Jun. 30, 2022

Related U.S. Application Data

(63) Continuation-in-part of application No. 16/989,607, filed on Aug. 10, 2020, now abandoned, and a continuation of application No. 16/681,109, filed on Nov. 12, 2019, now Pat. No. 10,773,097, and a continuation of application No. 15/677,840, filed on Aug. 15, 2017, now Pat. No. 10,525,278.

(51) Int. Cl.
*A61N 5/06* (2006.01)
*A61B 18/20* (2006.01)

(52) U.S. Cl.
CPC .......... *A61N 5/0617* (2013.01); *A61B 18/203* (2013.01); *A61B 2018/2065* (2013.01); *A61N 5/062* (2013.01); *A61N 2005/0652* (2013.01); *A61N 2005/0662* (2013.01)

(58) Field of Classification Search
CPC .................. A61N 5/0617; A61N 5/062; A61N 2005/0652; A61N 2005/0662; A61B 18/203; A61B 2018/2065
See application file for complete search history.

(56) References Cited

U.S. PATENT DOCUMENTS

| 2015/0224339 A1* | 8/2015 | Unger ................. A61N 5/0617 607/79 |
| 2016/0106999 A1* | 4/2016 | Michaels .............. A61M 37/00 604/20 |
| 2020/0221994 A1* | 7/2020 | Kumpan-Bahrami ...................... A61B 5/0002 |

* cited by examiner

*Primary Examiner* — Alyssa M Alter
*Assistant Examiner* — Jessandra F Hough
(74) *Attorney, Agent, or Firm* — Wasserbauer Law, LLC; Nicholas E. Blanton, Esq.; Damian G. Wasserbauer, Esq.

(57) ABSTRACT

The present invention relates to a light therapy apparatus, system, and method for providing light delivered to a body organ, e.g., skin such as a scalp, via one or more light guides in therapeutic dosages from one or more light sources operating in a variety of wavelengths. The light source may comprise one or more LEDs coupled to an illumination assembly, wherein an array of illumination assemblies may be coupled to a dome configured for conformal placement near or on a body organ. The plurality of illumination assemblies may be actuated upon by one or more actuators that form an active system to cause conformal contact with the body organ utilizing one or more actuator types. A control system may be operably connected to the plurality of illumination assemblies to control one or more parameters, such as localized light position and intensity, and activation of the actuators.

2 Claims, 15 Drawing Sheets

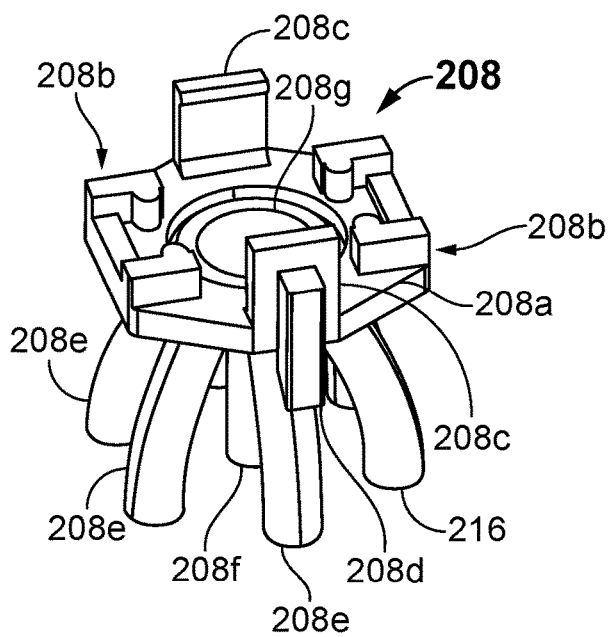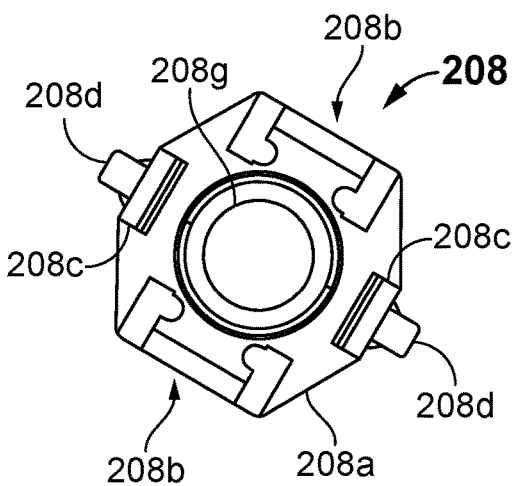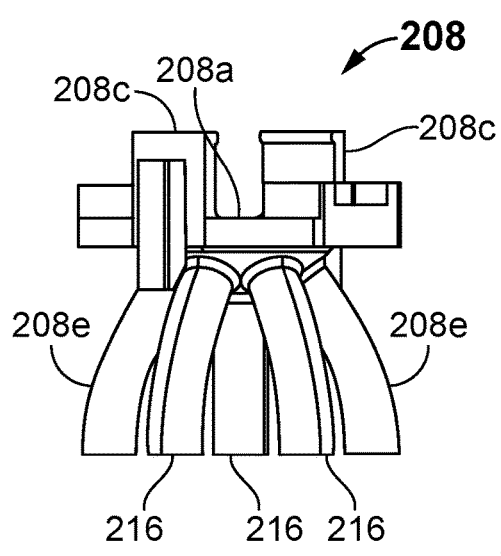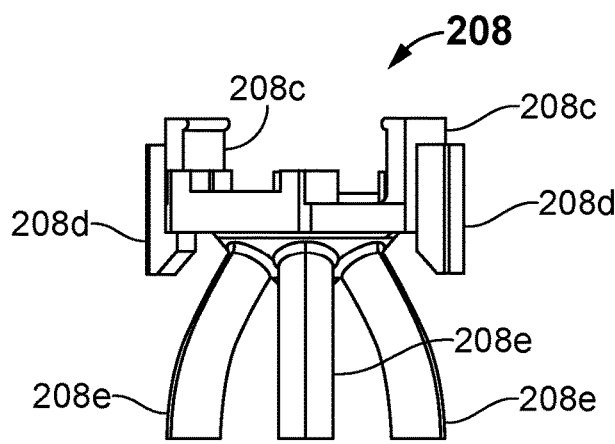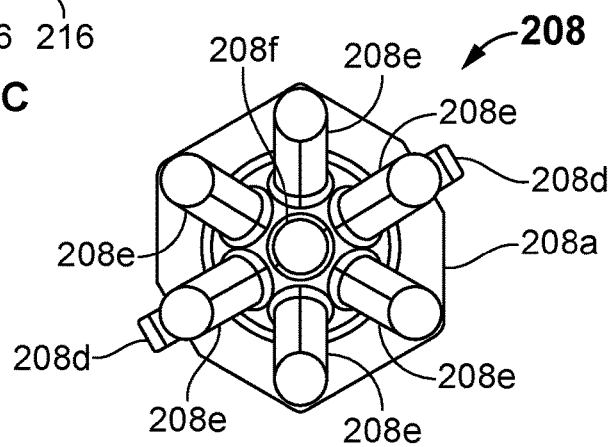
FIG. 4A
FIG. 4B
FIG. 4C
FIG. 4D
FIG. 4E

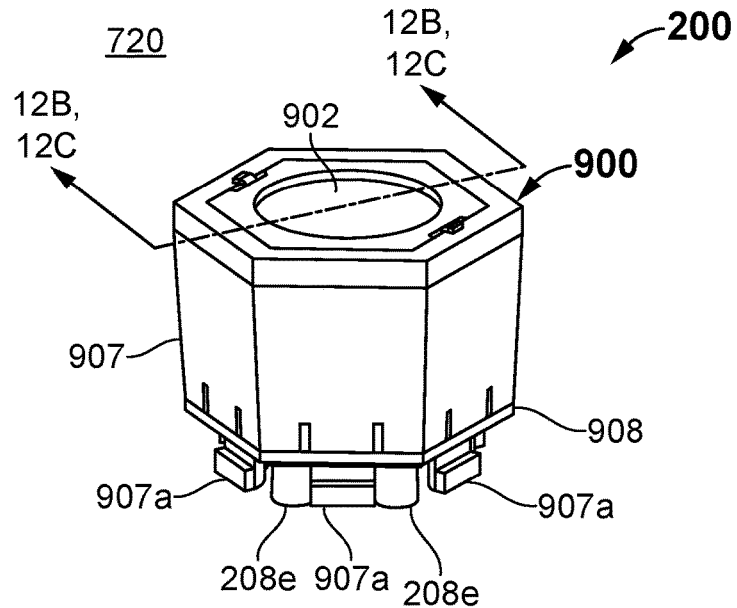
FIG. 12A
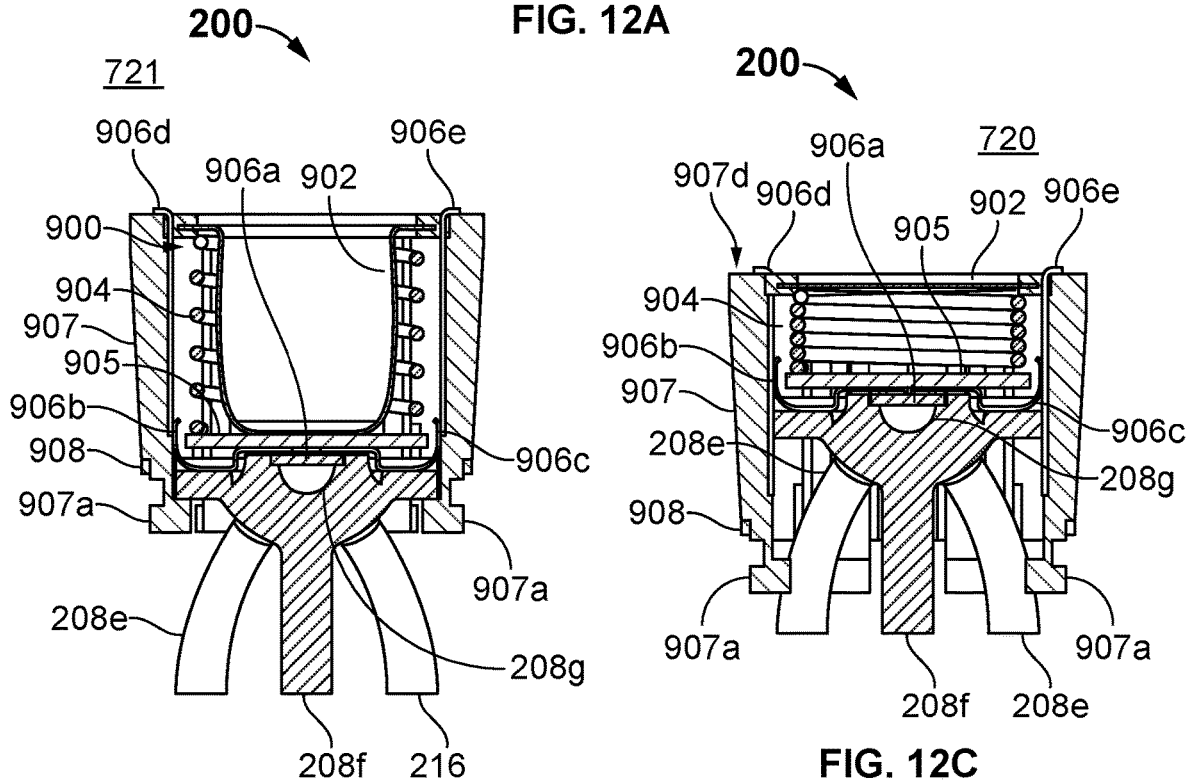
FIG. 12B
FIG. 12C

LIGHT BASED THERAPY DEVICES AND METHODS

RELATED APPLICATIONS

This application is a continuation-in-part of U.S. patent application Ser. No. 16/989,607 filed Aug. 10, 2020, which is a continuation of U.S. patent application Ser. No. 16/681,109 filed Nov. 12, 2019, now U.S. Pat. No. 10,773,097 issued Sep. 15, 2020, which is a continuation of U.S. patent application Ser. No. 15/677,840 filed Aug. 15, 2017, now U.S. Pat. No. 10,525,278 issued Jan. 7, 2020, which are incorporated herein by reference in their entireties.

BACKGROUND

The present invention relates to designs, systems, and methods of a light therapy device.

One major application of Low Level Light Therapy (LLLT) is to treat hair with photobiomodulation in the wavelengths of 614-624 nm, 668-684 nm, 751-772 nm, and 813-846 nm that has been proven to reduce inflammation in the scalp, stimulate the release of growth factors in the hair follicle, up-regulate the production of ATP (the energy source for the cell), and increase oxygen levels and blood flow via a vasodilatory effect. Devices of all sorts include caps, combs, helmets, handheld "massager-type" units, and hoods. These conventional devices have problems regarding hair absorption of the light intended for the skin and the reflective properties of the skin. Therapeutic dosing also is difficult as these two effects affect precise control thereof during therapeutic applications since the applied LLLT light can be scattered, absorbed, transmitted, or reflected. Consequently, there is a need for a LLLT device to overcome absorption and other problems to improve therapeutic dosing LLLT transmitted light applied to the surface for consistent dosing thereof.

SUMMARY

In one aspect, the present disclosure provides variations of improved systems, methods, and devices for providing LLLT devices. In one aspect, such devices are suited for hair growth by applying light delivery to the skin using one or more illumination sources. The present invention relates to a device for positioning over and applying electromagnetic energy to a body organ, the device comprising a dome forming a contoured shape, said dome including a plurality of dome openings, where an interior space of the contoured shape is adapted for placement over the body organ. The device may comprise a plurality of illumination assemblies each including an optical assembly having a proximal end optically coupled to a light source, a distal end configured to direct electromagnetic energy to the body organ, and a group of light guides therebetween, each of said illumination assemblies being coupled to the dome to allow the optical assembly to move freely through one of the dome openings. The device may use an actuator configured to move each optical assembly of the plurality of optical assemblies, upon activation, from a first position to a respective second position corresponding to a conformal arrangement around a body organ, and upon deactivation, to move the said plurality of optical assemblies back to said first position.

Variations of the device and system include illumination sources that are shaped for patient comfort and/or to distribute the light around the delivery or contact point. In additional variations, a projecting element that includes or carries the illumination source is actuated so as to allow conformal contact with the skin. An active system to cause conformal contact with the skin may include one or more actuation types, including but not limited to hydraulic, pneumatic, electrical, thermal, magnetic, and/or soft actuators. In an exemplary embodiment, an array of such projection elements having illumination sources are used to illuminate a substantial area of skin, such as the scalp. An advanced passive cooling scheme may be used to preserve the output power and efficiency of the light sources. Advantageously, the present invention delivers light directly to the skin, bypassing interference from hair follicles, thereby allowing for a known dosing intensity and distribution. The configurations described herein can provide an improvement in light delivery to the targeted region—one that reduces loss of energy to undesired absorption and reflection and that ensures maximum absorption by the target tissue, thereby enabling standardized dosing. Variations of the devices described herein can also allow delivery of light at or very close to the skin/scalp, which allows bypassing the interference that even short hair shafts above the skin create, and minimizing the effect of reflection. Additionally, the present invention may deliver light in one or more of the four optimum wavelength ranges.

Variations of the device also allow for a hands-free, cordless, and portable embodiments, with an interactive feedback component that allows a patient to monitor their progress, thereby further improving adherence with the treatment regimen. Such variations also time the treatments and help patients manage dosing frequency with a minimal amount of external visibility. Cell proliferation (i.e., growth of hair) is optimized with low doses over longer periods of time. So, the present LLLT device allows for convenient and frequent dosing (at least 2-3 times per week, if not daily).

Variations of the device also provide for different designs of biasing of an optical fiber assembly. In one aspect, a pressurized air bladder may exert a force at an end of each optical fiber assembly for a plurality of assemblies, so that each optical fiber assembly may independently conform to the scalp of a patient. Air pumps, valves, tubing and fittings may be used to complete a biasing system. In another aspect, a pressurized interstitial cavity may be provided to exert a force at an end of each optical fiber assembly for a plurality of assemblies, so that each optical fiber assembly may independently conform to the scalp of a patient. Similarly, air pumps, valves, tubing and fittings may be used to complete a biasing system.

Variations of the device additionally provide for ease of manufacturing, assembly, serviceability, and/or replacement of parts throughout the useful lifetime of the device. Such desirable effects may be achieved through minimization of parts, simplification of parts, and other novel approaches as described herein.

Other desirable features and characteristics will become apparent from the subsequent detailed description, drawings, and appended claims and/or abstract, when considered in view of this background and summary.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description of the Invention, which is to be read in association with the accompanying drawings, which are incorporated in and constitute a part of this specification, show certain aspects of the subject matter disclosed herein, and, together with the description, help explain some of the principles associated with the disclosed implementations, wherein:

FIGS. 4A through 4E are perspective, top, front, right-side and bottom views, respectively, of an optical assembly, according to an embodiment of the present invention;

FIG. 12A illustrates a perspective view of an illumination assembly thereof;

FIG. 12B is a cross-sectional view of the illumination assembly in an extended position, taken along lines 12C-12C of FIG. 12A thereof;

FIG. 12C is a cross-sectional view of the illumination assembly in a retracted position, taken along lines 12C-12C of FIG. 12A thereof;

DETAILED DESCRIPTION

Figure 1:
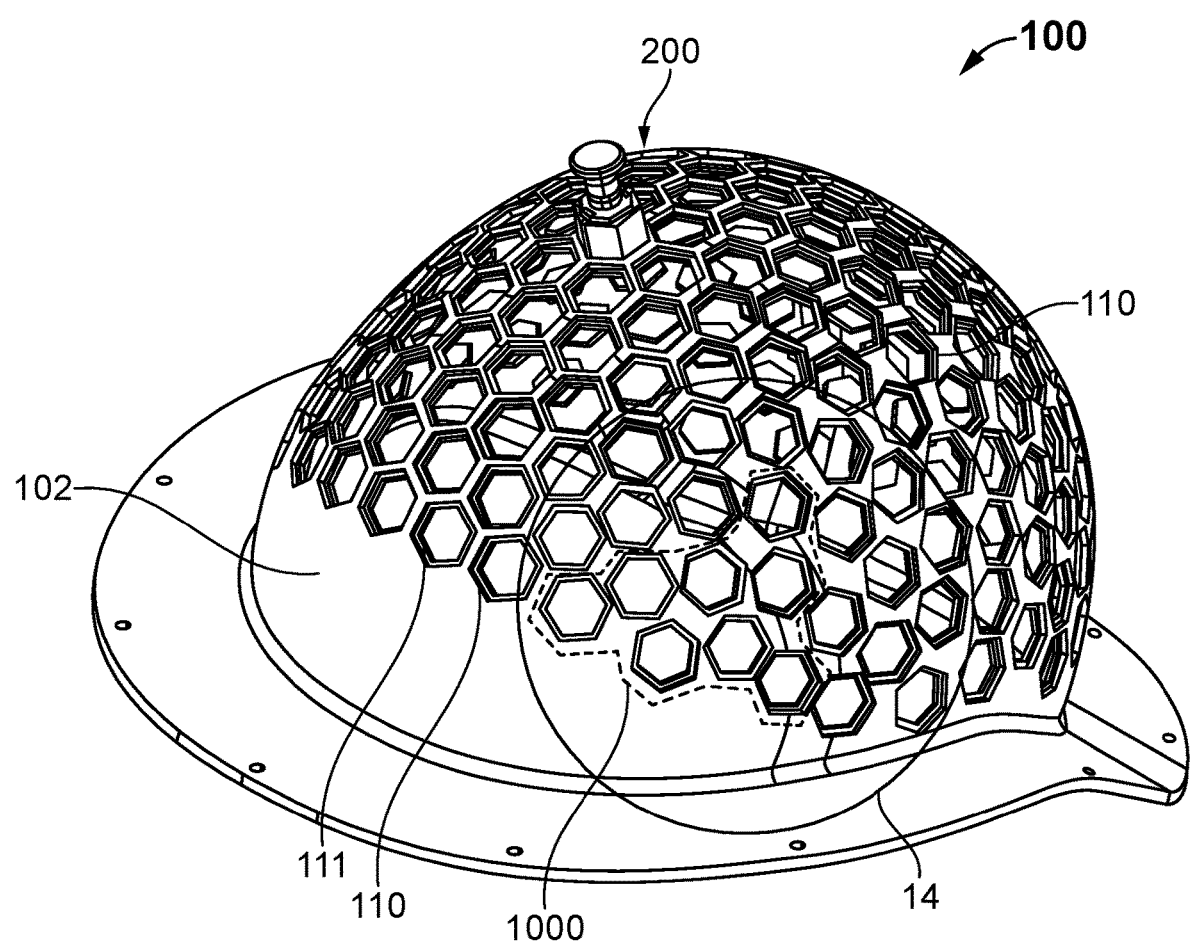
FIG. 1 illustrates a perspective view of a light therapy device for the scalp, including an illumination assembly and dome structure, according to an embodiment of the present invention.

Non-limiting embodiments of the invention will be described below with reference to the accompanying drawings, wherein like reference numerals represent like elements throughout. While the invention has been described in detail with respect to the preferred embodiments thereof, it will be appreciated that upon reading and understanding of the foregoing, certain variations to the preferred embodiments will become apparent, which variations are nonetheless within the spirit and scope of the invention. The drawings featured in the figures are provided for the purposes of illustrating some embodiments of the invention and are not to be considered as limitation thereto.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C." An exception to this definition will occur only when a combination of elements, functions, steps or acts are in some way inherently mutually exclusive.

The drawings featured in the figures are provided for the purposes of illustrating some embodiments of the present invention and are not to be considered as limitation thereto. The term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

Figure 15:
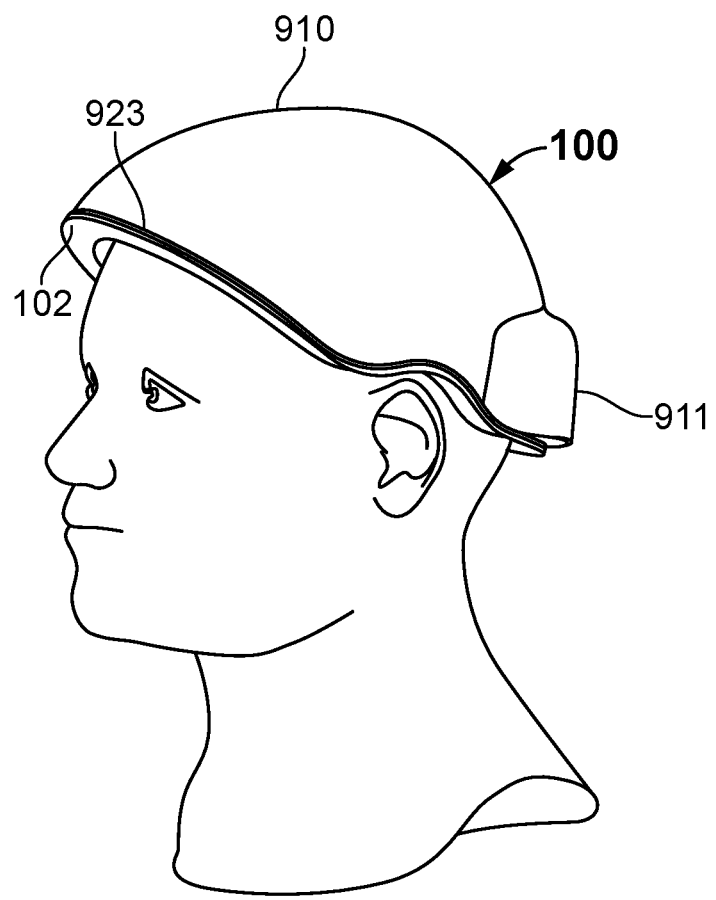
FIG. 15 is a perspective view illustrating systems and/or methods, used in an environment for LLLT illumination therapy and dosing of the scalp, of a light therapy product and or device being used by a patient, according to an embodiment of the present invention.

FIG. 1 provides a perspective view of an exemplary light therapy device, assembly, system and method for therapeutic treatment generally identified as element 100. The light therapy device 100 is described in an exemplary embodiment for therapeutic LLLT light therapy treatment of a scalp of a patient illustrating the concepts and features in the environment of the light therapy device worn on the head of the patient as shown, for example, in FIG. 15, although the particular features, structures, or characteristics may be combined in any suitable manner in one or more embodiments without limitation. An alternative embodiment for the light assembly of the therapy device 100, as shown FIGS. 11 and 12A-12C, is also within the scope of this disclosure for therapeutic LLLT light therapy treatment to a body organ. Other uses for therapeutic LLLT light therapy treatment can comprise the device 100 configured for an entirety of a body structure (such as a hand, leg, head, scalp, etc.) for treatment of the skin or tissue that is part of such a body structure.

Referring to FIGS. 1-15, the light therapy device 100 comprises a dome 102 configured with a plurality of openings 110 for a plurality of illumination assemblies 200. In certain figures herein, e.g., FIGS. 1-2, and 5-7, only one illumination assembly 200 is shown for the purpose of clarity. Generally, at least part of illumination assemblies 200 extend between an interior surface 104 and an exterior surface 106 of the dome 102. As noted herein, the illumination source 200 is adapted to transmit light to the tissue of the scalp from a source of illumination. Alternatively, or in combination, the light therapy device 100 comprises a singular assembly with an end, or a proximal portion, adapted to receive light energy from the source of illumination and transmit to the other end, or a distal portion, of the one or more projection elements configured to direct the electromagnetic energy to the body organ.

A plurality of openings 110 comprise a depression 111 formed along a portion of the exterior surface 106 of the dome 102. The depression 111 may be configured to receive an illumination assembly 200 and couple illumination assembly 200 to the dome 102 via a press fit, or through the introduction of an adhesive, or other coupling method, so as to facilitate manufacture, testing, assembly, repair, operation and/or use thereof. Furthermore, the openings 110 may be of a uniform hexagonal shape as shown in, for example, FIGS. 1, 2, 5-7, 10, and 14. The hexagonal shape generally serves to minimally conform to the plurality of auxiliary light guides 208e as shown in, for example, FIGS. 3, 5-6, 11, and 12A-120. The hexagonal shape may be configured to operatively connect the illumination assembly 200 to the dome 102 while inhibiting rotational displacement thereof. Alternatively, the illumination assembly 200, openings 110 and depression 111 may be formed in other shapes such as, for example, circular or generally polygonal in accordance with the number of auxiliary light guides 208e. For example, the illumination assembly 200 may be non-uniform in shape, and adapted for various localized regions of the dome structure 102; a variably-shaped illumination assembly 200 may be configured to cover or target patterns of alopecia as may be desired for a specific application. However, in the preferred embodiment, the hexagonal illumination assembly 200 advantageosly provides beneficial tissue coverage area, ease of manufacturing, replacement, and/or serviceability, while providing sufficient light therapy coverage over a treatment area and/or surface of the body organ in a substantially uniform manner.

Each of the illumination assemblies 200 are independently biased so that the tips 216 on the distal portion of the light guides, 208e, 208f, of each assembly can conform to the shape of the head and/or be operably in contact with the body organ. This biasing allows for an improved device with multiple illumination sources that achieves independent contact of each assembly to conform to a contoured surface of the body organ without significantly affecting adjacent assemblies, which increases the ability of the adjacent assemblies to irradiate the tissue, e.g., in a normal direction. Lambert's cosine law predicts that an illumination beam that is perpendicular to its target can achieve a higher rate of irradiance. In contrast, a beam that is offset from a perpendicular approach will have a greater degree of reflection off of the target area; so, an illumination beam will have the highest absorption for a curved or contoured body organ like the surface of the scalp, when that illumination irradiates to the scalp at a perpendicular angle. The independent biasing of the plurality of illumination assemblies, therefore, can decrease the overall reflectance of light from a curved surface and increase the effectiveness or uniformity of the applied LLLT light therapy. Consequently, the dome 102 advantageously maintains a normal orientation of each illumination assembly 200 as shown in FIG. 2.

Figure 2:
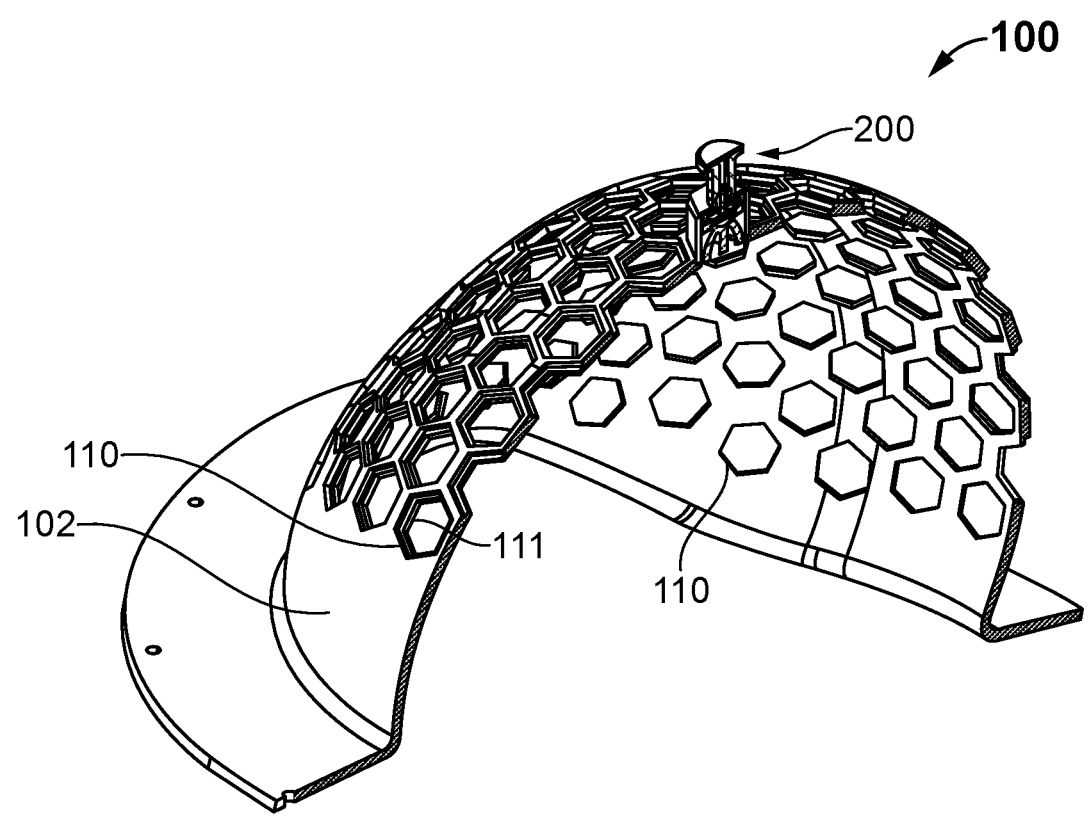
FIG. 2 illustrates a cross-sectional, perspective view of a light therapy device for the scalp, including an illumination assembly and dome structure, according to an embodiment of the present invention.
Figure 3:
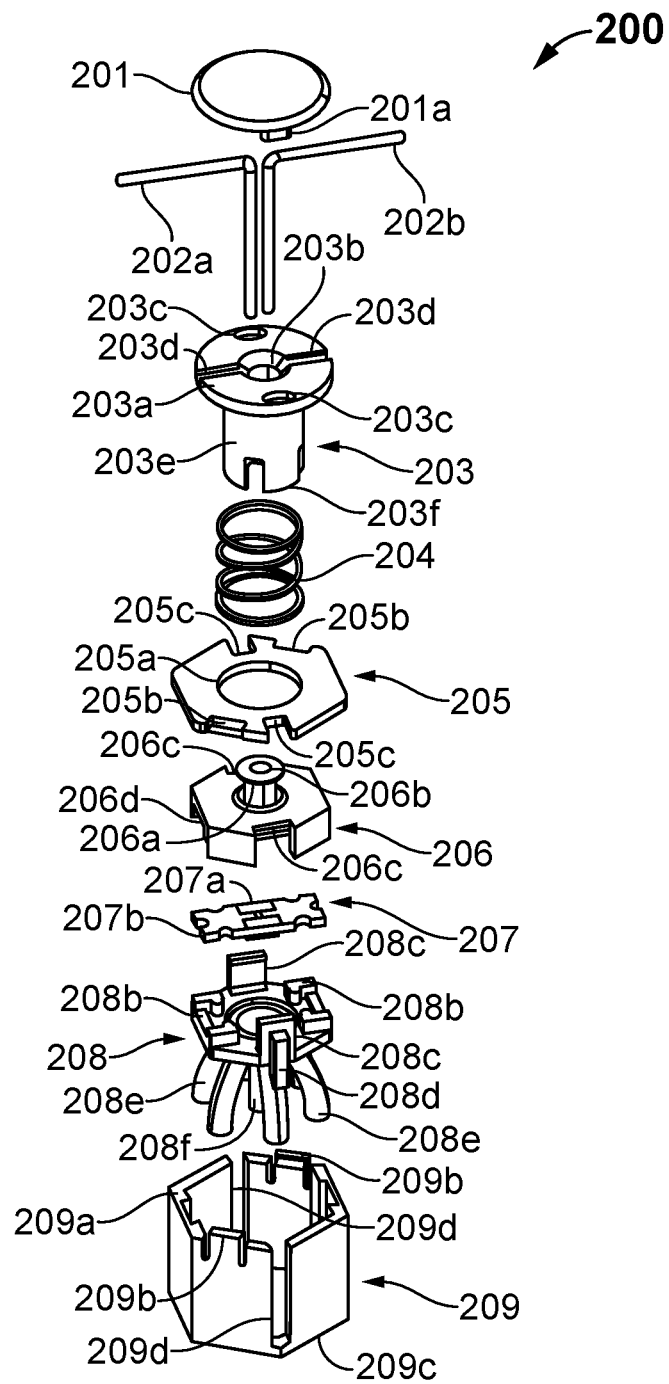
FIG. 3 illustrates an exploded view an illumination assembly, according to an embodiment of the present invention.

Referring to FIGS. 2 and 3, each illumination assembly 200 of the light therapy device 100 may comprise: a cap 201; first and second wires 202a, 202b; a body 203; a biasing element 204; a cover 205; a member 206; one or more light sources 207; an optical assembly 208; and a carriage 209. Body 203 may include a head 203a and a base 203e characterized in part by a body opening 203b, extending therethrough, configured to receive the first and second wires 202a, 202b. The head 203a may include one or more trenches 203d to allow the first and second wires 202a, 202b, to be wired to, or otherwise powered by, a source of electrical energy. Head 203a may further include tab receivers 203c, configured to couple to tabs 201a of cap 201. Cap 201 may be formed flat to facilitate a force imparted thereon; alternatively, cap 201 may be configured with a fastening element to couple illumination assembly 200 to an actuator, such as interstitial reservoir 700 described herein. Tabs 201a and tab receivers 203c may further serve to keep the wires, and other components of the illumination assembly 200, in place when no force is present. In this manner, cap 201 may be disposed flush with the head 203a of body 203 to transmit a force from the top of cap 201 through to base 203a and to associated components coupled thereto. Base 203a may be cylindrical or otherwise configured to receive a biasing element 204, with the bottom-side of head 203a serving as an abutment, or a surface, for the biasing element 204 to exert a reaction force thereon. Additionally, base 203e may include a receiver 203f at an opposite end of the heat 203a, the receiver 203f configured to receive a plug 206a of member 206. Importantly, the biasing element 204 may be a spring, or any other elastic component that can absorb potential energy and return the device back to a resting position, such as an elastomer.

Figure 5:
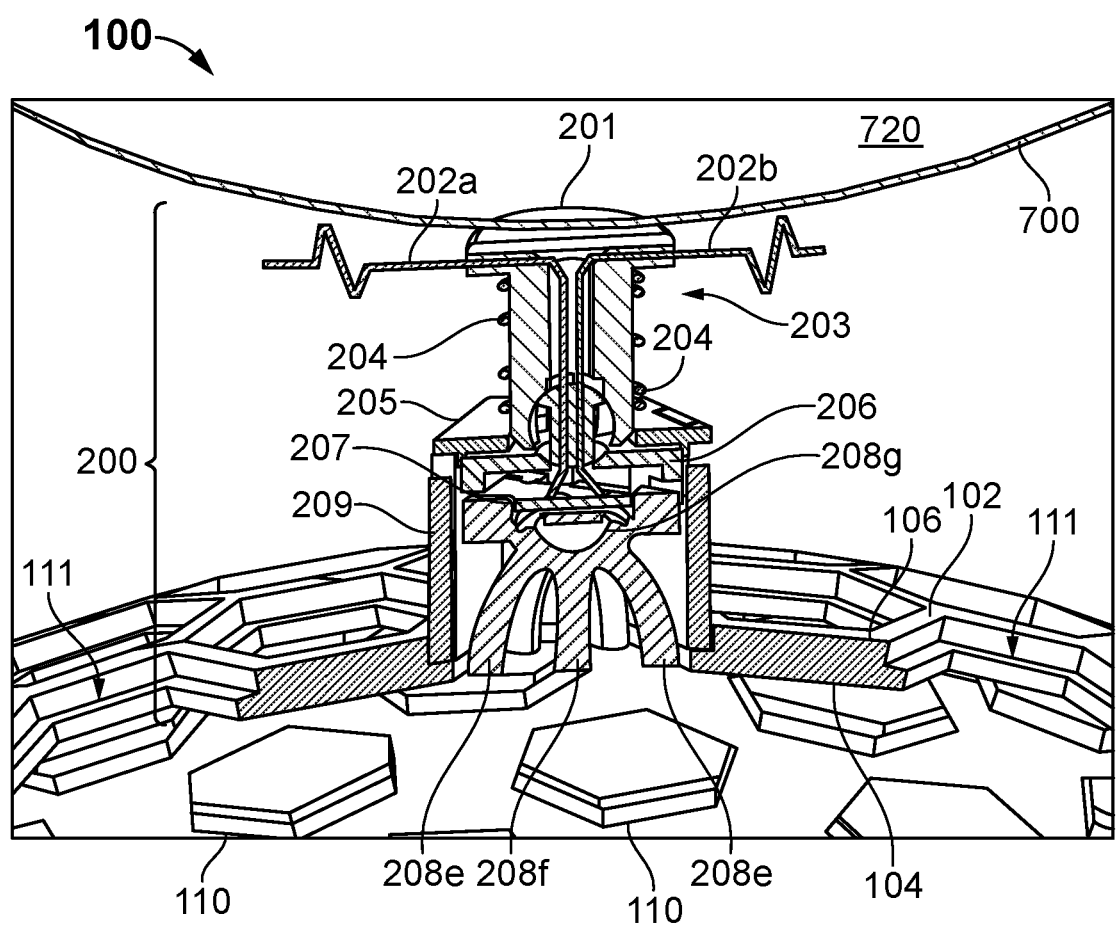
FIG. 5 illustrates a cross-sectional, perspective view of a light therapy device for the scalp, including an illumination assembly and dome structure, wherein the illumination assembly is shown in a first, or retracted, position, according to an embodiment of the present invention.

Referring FIG. 3, the cover 205 may comprise a cover opening 205a, one or more latch receivers 205b, and one or more cover slots 205c. Cover opening 205a may be configured as a circular opening having a sufficient dimension large enough to allow the base 203e of the body 203 to pass therethrough unimpeded, as well as dimensioned smaller than the circular opening to hold the biasing element 204 such that the biasing element 204 does not bypass the cover 205. Therefore, cover 205 provides a complementary abutment or surface for the biasing element to return the illumination assembly 200 to a first position, e.g., a retracted position as shown in FIG. 5. One or more latch receivers 205b may be configured to receive one or more carriage flanges 209b of carriage 209. One or more cover slots 205c may be configured to ensure that the cover 205 does not interfere with the one or more protrusions 208d as the optical assembly 208 translates within carriage 209 during operation to/from the second position, or extended position, the second position being shown in, e.g., FIG. 6. Additionally, latch receiver 205b and/or cover slots 205c may be utilized to orient cover 205 with respect to the rest of the illumination assembly 200, advantageously for ease of assembly and/or repair of light therapy device 100.

Referring FIGS. 3 and 4-6, the member 206 may comprise a plug 206a, one or more wire opening 206b passing therethrough, one or more upward flange receivers 206c, and one or more slotted portions 206d. The member 206 may be configured to couple to body 203 via plug 206a such as, for example, by snap-fitting, press-fitting, gluing, or otherwise adhering the same to receiver 203f by known manufacturing methods. The one or more wire openings 206b may have an electrical circuit connection configured by hard-wiring to a light source 207 via wires 202a, 202b. The one or more upward flange receivers 206c may be configured to receive the one or more upward flanges 208c of the optical assembly 208. For ease of manufacturing, optical assembly 208 may be an article of manufacture comprising a base 208a, a light source receiver 208b, one or more upward flanges 208c, one or more protrusions 208d, one or more auxiliary light guides 208e, a central light guide 208f, and a lens 208g.

Light source receiver 208b, upward flanges 208c, protrusions 208d, and light guides 208e, 208f may be formed on base 208a; lens 208g may be formed within, or constitute a central portion of, said base 208a. As previously mentioned, one or more upward flanges 208c may be configured to couple the optical assembly 208 to member 206 along upward flange receiver portions 206c formed thereon. Light source receiver 208b may extend outwardly from the base 208a and may be configured to receive a light source 207, the light source 207 having a complementary shape so that light may be directed to the lens 208g and transmit light energy to individual light guides 208e and 208f. The protrusions 208d may extend outwardly from a portion of said upward flanges 208c and/or said base 208a, and may be configured to maintain an orthonormal position of the tips 216 of the light guides 208e, 208f, with respect to the carriage 209 and dome 102, as the optical assembly 208 translates within carriage 209 during operation to/from the second position, or extended position, the second position being shown in, e.g., FIG. 6. Similarly, the shape of the body 208a may be formed in a complementary shape to that of the interior of the carrier 209; e.g., one or more slots 209d of carriage 209 may complement protrusions 208d such that rotation of the inner assembly, i.e., optical assembly 208 with respect to the carriage 209 does not occur. At the same time, the respective sizes of components comprising member 206 and optical assembly 208 are configured to allow free movement, e.g., smooth or otherwise uninhibited translation, of the same within the carriage 209 from the first position, as shown in FIG. 5, to the second position, as shown in FIG. 6, and any position therebetween.

Figure 6:
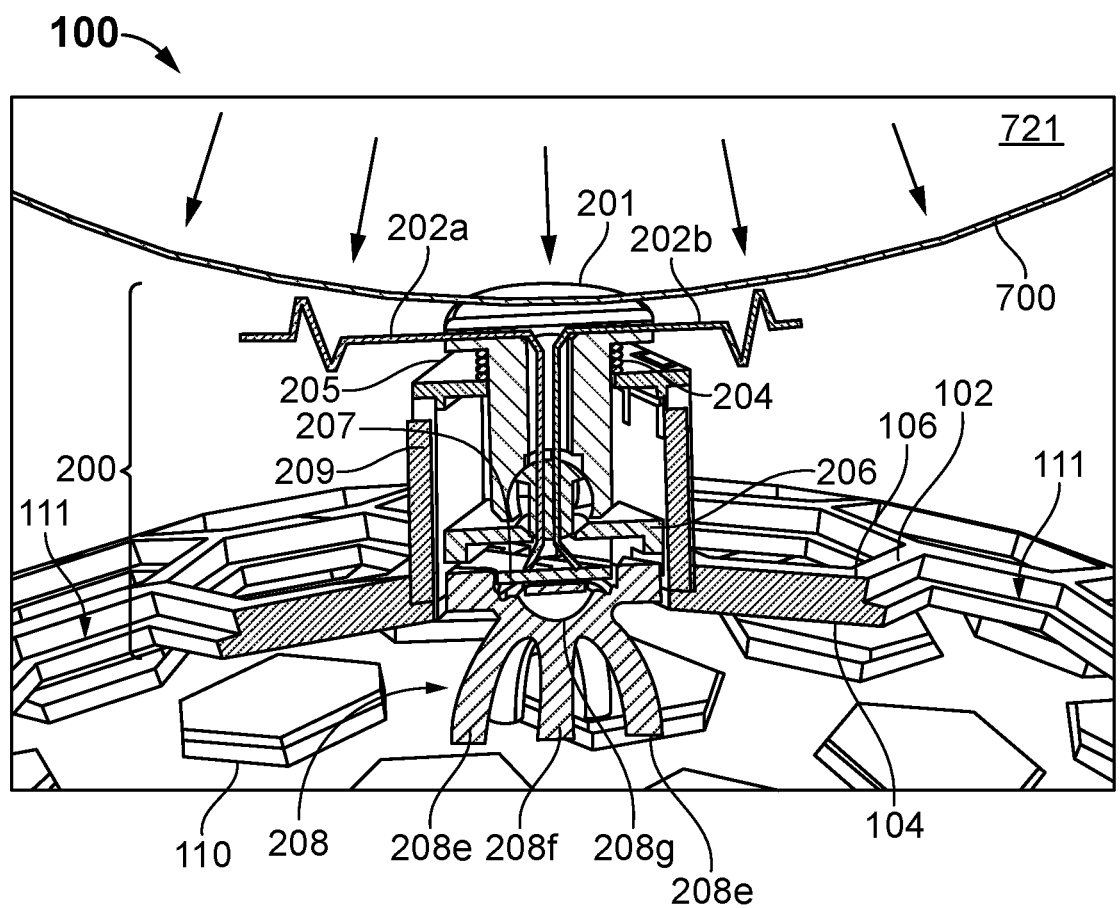
FIG. 6 illustrates a cross-sectional, perspective view of a light therapy device for the scalp, including an illumination assembly and dome structure, wherein the illumination assembly is shown in a second, or extended, position thereof.

Referring to FIGS. 5 and 6, a concave shape of lens 208g is configured to transmit and refract efficiently at the barrier so that light passes from the illumination source to the plurality of light guides 208e, 208f. As shown, for example, in FIGS. 4B and 5-6, the concave shape of lens 208g helps transmit and refract light from one or more light sources 207 to each of a plurality of light guides 208e, 208f, such that optical assembly 208 optimizes the light output of said light guides to the scalp and/or body organ. The auxiliary light guides 208e and central light guide 208f may be arrayed such that each guide is normal to the corresponding curved surface of the lens 208g at each localized position. In operation, the light emitted from light source 207 may then be guided down the length of each guide to a tip 216, where the light may then be transmitted to the body organ, e.g., scalp. The guiding of such light occurs by internal reflections off the light guide surface, boundary, and/or a reflective coating along each length. As shown in FIGS. 4C and 4D, the tips 216 are adapted to redirect emitted light in a configuration consistent with the principles of Lambert's cosine law and desired effect thereof. The hexagonal shape of the openings 110 of the dome 102, the required number and/or quantity of light guides may vary by application from one to a plurality. The arrangement of the plurality of light guides 208e, 208f and light sources disposed at proximal portion or end(s) opposite to tips 216 are configured to capture a maximum amount of light emitted from the light source 207 to the lens 208g. Moreover, flanges 208c disposed at these ends at the location of the base 208a, may facilitate maximizing this transmission, as well as provide additional strength at the light guide/base junction to minimize breaks of the light guides 208e, 208f.

Referring to FIGS. 3-6, a carriage 209 may comprise a first end 209a, one or more carriage flanges 209b formed therealong, a second end 209c, and one or more slots 209d extending downwardly from said first end 209a. As previously mentioned, carriage 209 may form a hexagonal shape to complement movement of optical assembly 208 therein, and to complement rigid coupling to dome 102 along depression 111. Alternatively, the carriage 209 may be formed alone, or in combination, in a circle or polygon shape. The shape selection derives from the number and arrangement of light guides, and may be formed to suit similar purposes, such as obtaining adequate coverage, and formed to provide consistent light coverage across the body organ. Additionally, in an alternative embodiment hereof, the carriage 209 may house electrical components to eliminate wiring structure throughout the interstitial space 730 shown in FIG. 7 by forming electrical connections and/or circuit components formed integral or on the dome 102.

Figure 11:
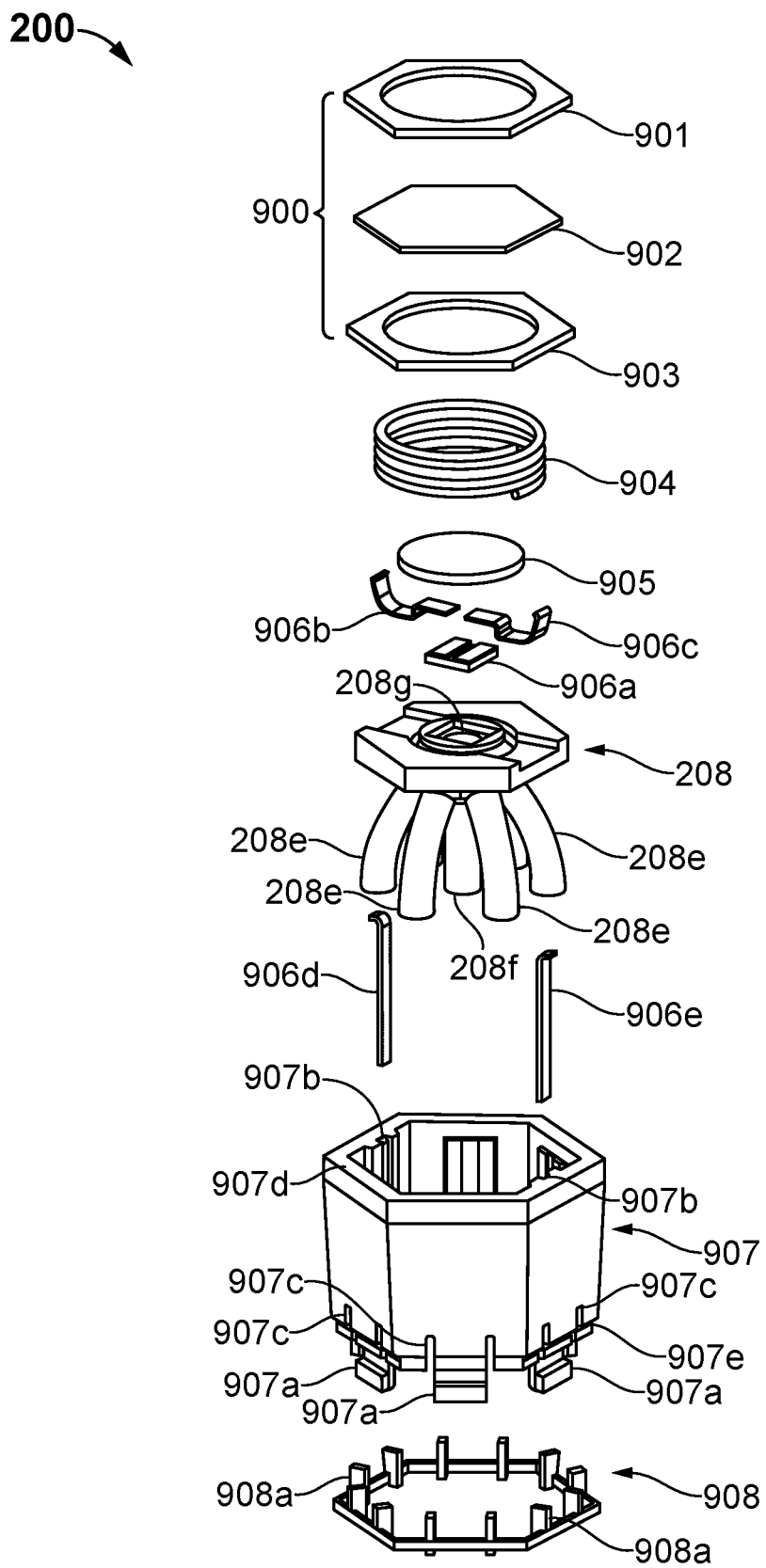
FIG. 11 illustrates an exploded view of an illumination assembly thereof.

Referring to FIGS. 3, 5-6, as well as a light-emitting diode (LED) 906a of an alternative embodiment illustrated in FIGS. 11 and 12B-12C, the light source 207 may comprise a light-emitting diode (LED) 207a coupled to a PCB board 207b. The PCB board 207b may be configured to accept first and second wires 202a, 202b, to power 207a and also to provide a structure to securely couple the light source 207 to the optical assembly 208 such as, for example, via light source receiver 208b. FIG. 3 further illustrates that the PCB board 207b may be formed as a complementary shape to the features formed in the light source receiver 208b, for snap-fitting light source 207 into place, and for stability in operation.

Regarding the LED 207a, as shown in FIG. 3, and LED 906a shown in FIG. 11, the light emitting diode may be constructed from suitable materials for the purpose of photobiomodulation, whereby the light sources can be selected to provide light energy in a wavelength(s) of 614-624 nm, 668-684 nm, 751-772 nm, and/or 813-846 nm, and other equivalent wavelengths beneficial for LLLT light therapy are considered to be within the scope of this disclosure. In particular, light sources operating at wavelengths of 668-684 nm have been shown to produce an uptick in energy of the body organ, whereas light sources operating at wavelengths of 813-846 nm have been shown to produce an increase in circulation of the body organ, e.g., each therapeutically beneficial for hair follicle growth. However, any light range that achieves a notable result falls within the scope of this disclosure; for example, the ranges 614-624 nm AND 751-772 nm may be utilized herein. Furthermore, known LED products are available which are capable of operating to produce light at two separate wavelength bands, i.e., at 668-684 nm and 813-846 nm, simultaneously, and such LEDs are considered suitable for use with the light therapy device 100. Similarly, with respect to the arrangement of light sources across the entire dome 102, any combination of useful operating conditions may be employed, including but not limited to: LEDs operating at one or more wavelength bands corresponding to a single string of LEDs wired and controllable together; LEDs operating at one or more wavelength bands corresponding to a known localized alopecia pattern; LEDs operating at one or more wavelength bands corresponding to a desired light output intensity at a localized area, distinguishable from LEDs operating at one or more wavelength bands corresponding to a separate, localized area; and LEDs operating at one or more wavelength bands at a localized area, distinguishable from LEDs operating at one or more wavelength bands corresponding to a separate, localized area.

Figure 13:
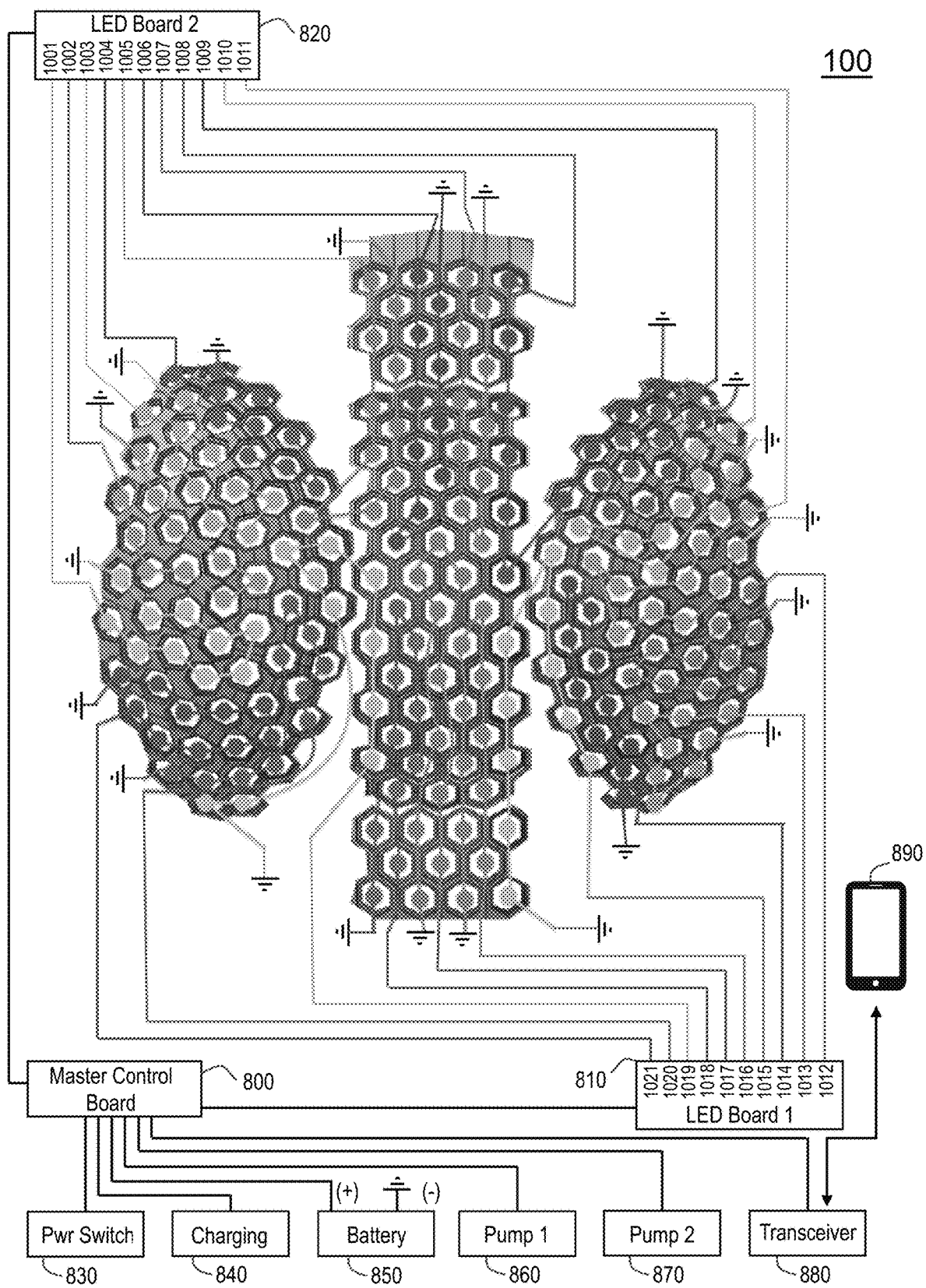
FIG. 13 is a schematic diagram view illustrating a control system according to an embodiment of the present invention.

Furthermore, illumination intensity may vary according to the desired outcome of hair restoration, as may be deemed appropriate. Here, it is contemplated that the duration of a light therapy session, and/or the intensity of the illumination emitted during that duration, may vary. Optimal treat schedules may vary according to the patient's initial conditions with respect to the location and severity of alopecia on the body organ, and may also vary according to how the patient responds over time to said treatment, as determined by the physician, the patient, etc. Such scheduling may be facilitated through integration of one or more external wireless communication devices, such as a smartphone 890 as shown in FIG. 13. Scheduling, illumination intensity, and the like are further described below in relation to, e.g., the controls aspects demonstrated in FIG. 13.

Referring now to FIGS. 5 and 6, an illumination assembly 200 is shown in operation, illustrating a first position or retracted position 720 and a second position or an extended position 721, respectively. An actuator, such as an interstitial reservoir 700 is shown disposed above cap 201 of the illumination assembly 200. Upon actuation, the interstitial reservoir 700 may impart a force on cap 201, represented by vectors acting downwardly as shown in FIG. 6. In another sense, FIG. 5 represents a first position 720 where the biasing element 204, e.g., a spring, is substantially in a resting state/position. Referring to FIG. 6 illustrating a second position 721 where the biasing element 204 has stored some amount of potential energy, corresponding to some amount of linear deflection or translation imparted on the actuator system of the device from an external source, such as an interstitial reservoir 700, such that upon removal of the external source, the device reverts back to the first position 700, as the biasing element 204 converts potential energy to kinetic. This may also be described as a forward/backward, or an upward/downward motion that independently moves each of the light sources to the body organ, e.g., scalp, when the device is turned on, and moves each of the light sources away from the body organ, when the device is turned off. Any mechanism may be used to impart a force upon illumination assembly 200 such that movement from the first position 720 to the second position 721 may be achieved.

Actuation of a plurality of illumination assemblies 200 may occur independently, or simultaneously, i.e., actuated from a common actuator system. The objective of the actuation is to conform to the unique contours of an individual's body organ, and therefore, light therapy device 100 is purposed to achieve that objective. Generally speaking, an actuator, whether independent or simultaneous, imparts a force sufficient to overcome the counter force of the biasing element to move the optical assembly 208 distally toward the body organ and conform thereto; the distance of translation of one illumination assembly 200 as compared to another illumination assembly 200 may therefore differ, or be more-or-less the same, depending on the contours of the patient's body organ. In the context of the scalp, when the user first puts on the light therapy device 100, the device 100 may be loose around the patient's head; when the user turns the device 100 ON, the device may subsequently create a tighter fit around the patient's head, corresponding to the independent, or otherwise appropriate, gentle translation of a plurality of illumination assemblies 200 toward and around the patient's scalp. Upon completion of the therapy/treatment session, i.e., when the device turns OFF, the device 100 will again loosen around the patient's head, to allow the patient to remove device 100.

In an alternative embodiment, actuation of illumination assembly 200 may be achieved by a different actuator system. It should be noted that alternatives for a pneumatic actuator system are discussed in detail in this disclosure with respect to FIGS. 8A-9C. As an alternative example, a hydraulic actuator may be used to impart a force or exert a pressure on cap 201 or associated components. A hydraulic actuator may further assist with heat dissipation caused by light generation. Alternatively, an electrical actuator may be similarly used, which may comprise individual solenoids located proximate each illumination assembly 200. An electric motor, or a piezoelectric material, and/or a comb drive may be similarly situated to actuate each illumination assembly 200. Other alternatives contemplated herein include thermal actuators, magnetic actuators, and soft actuators, such as, for example, a shape memory alloys and/or polymer. Design considerations concerning selection of one or more actuator types generally include the amount of force and/or pressure exerted on an illumination assembly 200, wherein sufficient force may be provided to overcome the retractive force of the biasing element, but also where the force maintains a maximum threshold so as to not cause trauma or discomfort to the patient. In this manner, any actuator suitable for this purpose is contemplated to fall within the scope of this disclosure, wherein said actuator may be considered as a device which converts an input energy or motion to a controlled output motion in order to accurately position a load and return it to the original position.

As shown in FIGS. 5 and 6, first and second wires 202a and 202b may be disposed above the carriage 209 and configured with the LEDs 207a or 906a wired in series to exhibit constant current, and/or LEDs 207a or 906a wired in parallel to exhibit constant voltage. As shown diagrammatically in FIG. 13 or 14, a plurality of LEDs 207a or 906a may comprise a single zone, or string, are wired in series. Therefore, according to the embodiment of FIGS. 5 and 6, the wires 202a, 202b, extending out of the head 203a of body 203 may be wired on either side of illumination assembly 200 to electrically couple to an adjacent illumination assembly; if at an end of the string, or if only one LED is on a string, one wire may be wired to/from a controller and another wire to/from the ground. In an alternative embodiment, in accordance with that shown and described with respect to FIGS. 10-12C, all of the electrical wiring may be moved from the interstitial space 730 and integrally configured with components, or alternatively by flexible circuit disposed on the dome for electrical connections between the illumination assembly 200 and/or dome 102. Advantageously, manufacturing of the light therapy device 100 with either wiring configuration may be used and are interchangeable throughout in the various embodiments of the invention.

Figure 7:
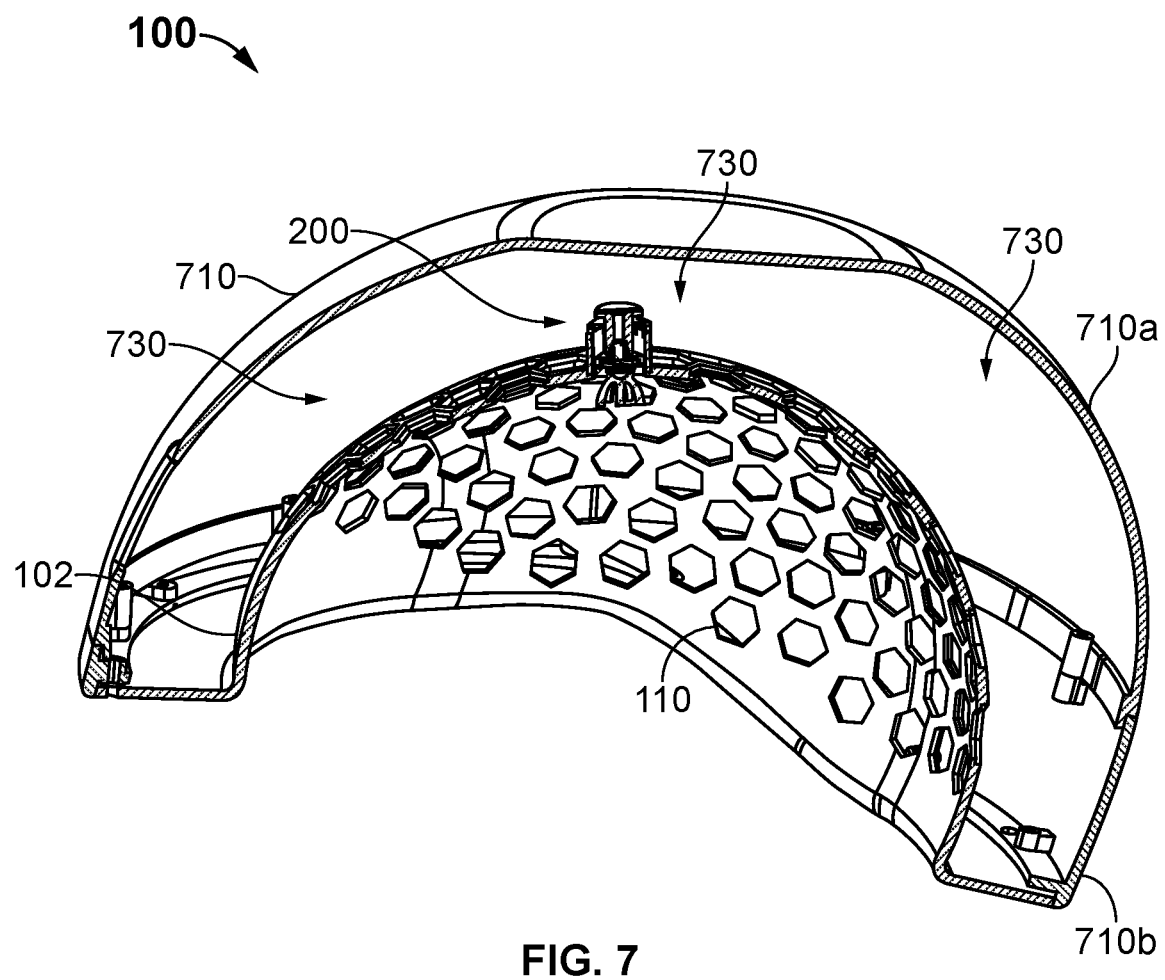
FIG. 7 illustrates a perspective view of a light therapy device with an illumination assembly, dome structure, and outer shell according to the invention, according to an embodiment of the present invention.

As shown in FIG. 7, the dome 102 and plurality of illumination assemblies 200 may be surrounded by an outer shell 700 comprising an upper portion 710a and a lower portion 710b. Again, only one illumination assembly 200 is shown for clarity. The brim portion of dome 102 may couple to lower portion 710b. An interstitial space 730 may be formed between the plurality of illumination assemblies 200 and an inner surface formed by outer shell 700. The interstitial space 730 may be configured to house an interstitial reservoir 700 that may be configured to actuate one or more illumination assemblies 200. Electronics, including control boards, as well as pumps and the like (not shown) may be conveniently located in the interstitial space along the brim of dome 102 near lower portion 710b, arranged according to the allowance of space and/or advantageously located proximate or adjacent to other components coupled to the instant component. To a similar effect, electronics may be distributed to facilitate proper weight balance of the light therapy device 100 and associated components therein, such as when device 100 is in use, e.g., placed on the head of a patient.

Figure 8A:
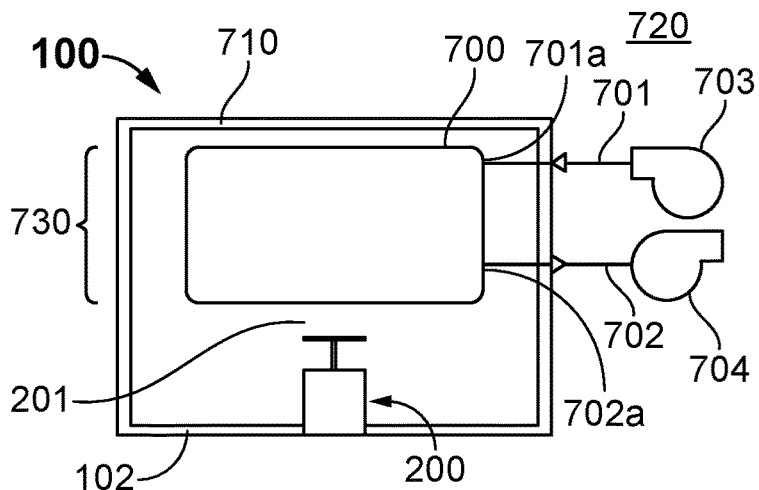
FIG. 8A is a schematic view of a fluid system diagram illustrating the system in an unpressurized position, an OFF position, and/or a battery charging position thereof, according to an embodiment of the present invention.
Figure 8B:
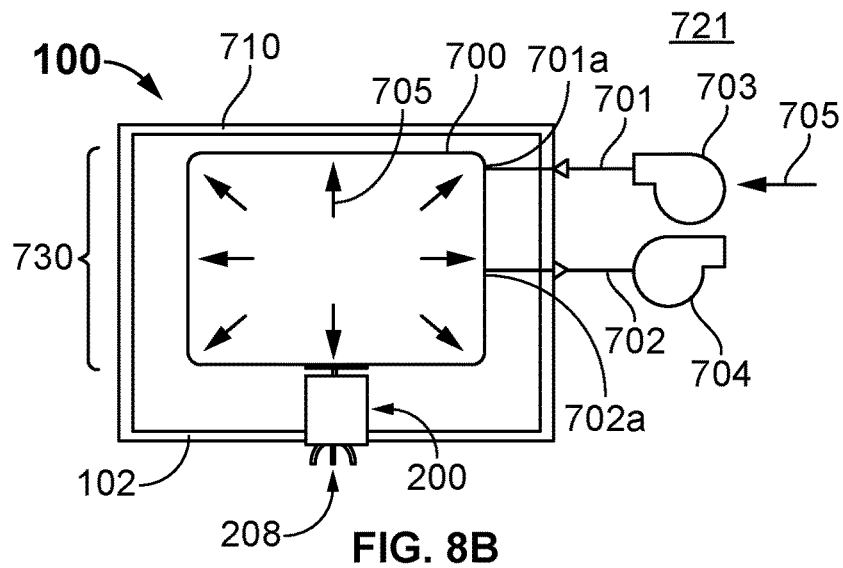
FIG. 8B is a schematic view of a fluid system diagram illustrating the system in a pressurized position, a pressurizing position, and/or an ON position thereof.
Figure 8C:
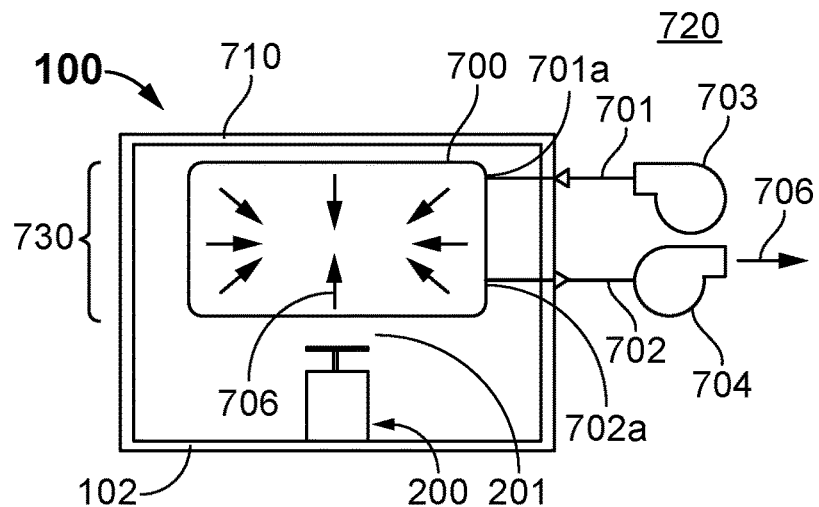
FIG. 8C is a schematic view of a fluid system diagram illustrating the system in a depressurized position, a depressurizing position, and/or a POWERING DOWN mode thereof.

Referring now to FIGS. 8A-8C, according to an embodiment, diagrams of an interstitial reservoir 700 are shown in the context of a light therapy device 100. Similar to FIG. 7, interstitial reservoir 700 may be disposed within interstitial space 730. The interstitial space 730 may be further characterized by outer shell 710 coupled to dome 102 as represented diagrammatically herein. Interstitial reservoir 700 may include an inlet portion 701, an outlet portion 702, an inlet pump 703, and an outlet pump 704. Inlet portion 701 may include an intake 701a, and outlet portion 702 may include an outtake 702a. Intake and outtake 701a, 702a may take the form of valves that inhibit the flow of fluid through inlet and outlet portions 701 and 702, respectively. These valves may be active components, such as actuated ball valves, they may be passive components, such as backflow preventer valves, or any combination thereof. Furthermore, these valves need not necessarily be located at the junction between the interstitial reservoir 700 and the intake/outtake 701a, 702a, but may be located in any appropriate position within the fluid system.

First according to FIG. 8A, in a resting or OFF position, an exemplary illumination assembly 200 is shown with the optical assembly 208, cap 201, and associated components in a retracted position. This may also be referred to as a first position 720. This corresponds to when the light therapy device 100 is stored or otherwise not in use. Second according to FIG. 8B, in an operational or ON position, inlet pump 703 accepts an infiltrated fluid 705, causing interstitial reservoir 700 to exert a pressure on cap 201, thereby moving optical assembly 208 to an extended, or second position 721. This principle may be extended across all illumination assemblies 200, where interstitial reservoir 700 is suited to provide the pressure necessary for the light therapy device 100 to conform to the unique contours of an individual's body organ, e.g., scalp. During operation, pump 703 may work to maintain an appropriate internal pressure to achieve this effect; similarly, intake and outtake 701a, 702a may inhibit exfiltrated air flow; or, a combination of these components may achieve this result. Third according to FIG. 8C, when a light therapy session has been completed or OFF position occurs, outlet pump 704 may work to pump exfiltrated air out of interstitial reservoir 700, thereby returning illumination assembly 200 to a first position 720 wherein optical assembly 208 resumes a retracted position. In an alternative embodiment, the fluid system described herein may omit certain components; for instance, a simple pressure release valve, e.g., outtake 702a, may be utilized exclusively to return the light therapy device 100 back to a first position 720, thereby removing the outlet pump 704 from the system. In yet another alternative embodiment, a plurality of interstitial reservoirs 700 may be disposed within light therapy device 100. These may serve to actuate a localized region, suitable for an intended purpose, such as to vary the amount of pressure exerted on a subset of illumination assemblies 200, thereby providing a desired translation corresponding to said second position 721 of that subset, relative to another subset of illumination assemblies 200.

In an alternative embodiment represented in FIGS. 9A-12C, interstitial reservoir 700 is omitted from the fluid system design, and is replaced by the container formed by outer shell 710 and dome 102, diagrammatically shown herein. Here, FIGS. 9A-9C correspond to like physical conditions as those described with respect to FIGS. 8A-8C. And as before, various combinations of representative components may be included to acuate one or more illumination assemblies 200. In to this embodiment, the pressurized cavity formed by outer shell 710 and dome 102 may receive infiltrated fluid or exfiltrated fluid via intake 701a and outtake 701b, respectively. These ports may act in conjunction with, or in lieu of, pumps 703, 704, or in any combination thereof to pressurize and/or depressurize interstitial space 730. As will be elaborated upon below, illumination assemblies according to this embodiment may employ the use of a localized, flexible and/or elastic membrane in lieu of cap 201 and associated components. Therefore, as shown in FIG. 9B, when interstitial space 730 becomes pressurized via introduction of infiltrated air 705, or as interstitial space 730 becomes pressurized, a flexible membrane will elastically deform, thus displacing optical assembly 208 from a retracted/first position 720 to an extended/second position 721. By a similar token, depressurization returns illumination assembly 200 to the first position 720.

Figure 9A:
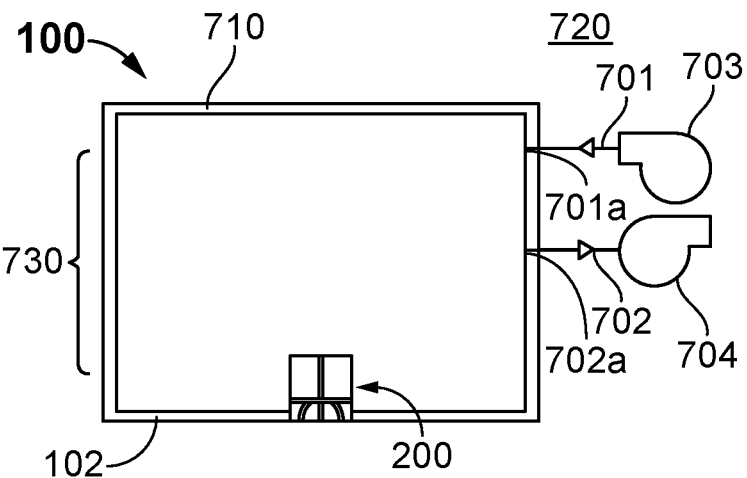
FIG. 9A is a schematic view of a fluid system diagram illustrating the system in an unpressurized position, an OFF position, and/or a battery charging position thereof, according to an alternative embodiment of the present invention.
Figure 9B:
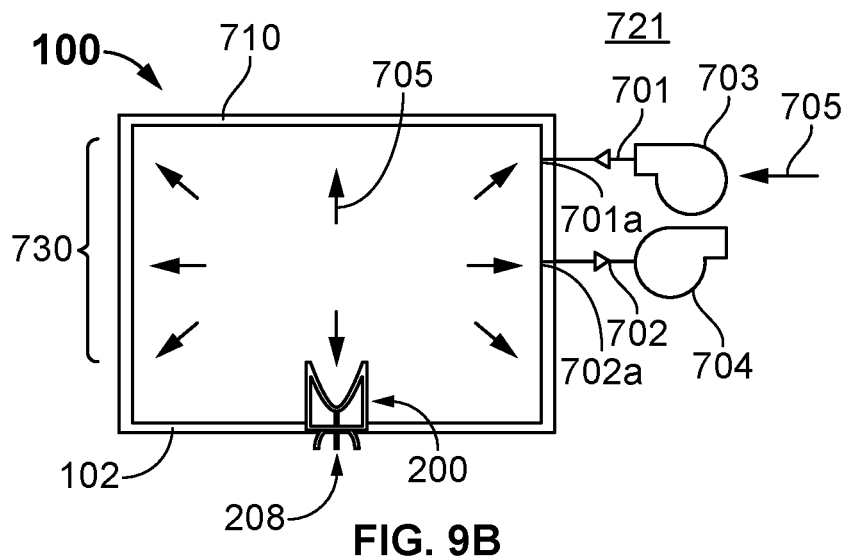
FIG. 9B is a schematic view of a fluid system diagram illustrating the system in a pressurized position, a pressurizing position, and/or an ON position thereof.
Figure 9C:
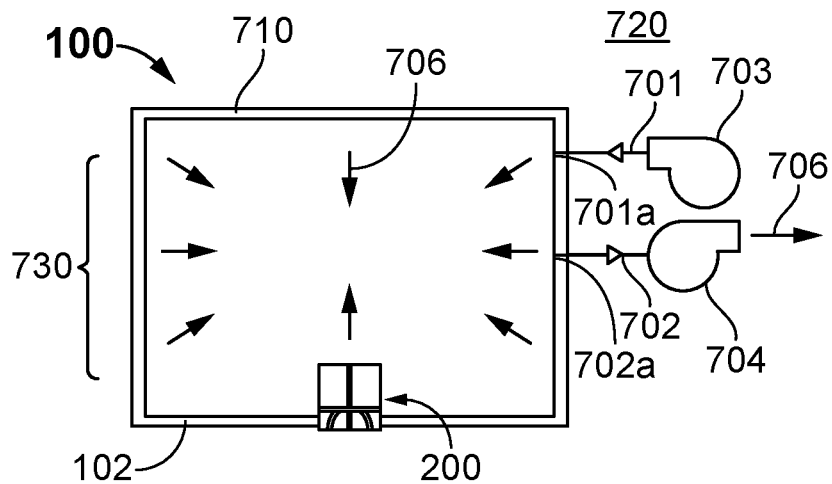
FIG. 9C is a schematic view of a fluid system diagram illustrating the system in a depressurized position, a depressurizing position, and/or a POWERING DOWN mode thereof.
Figure 10:
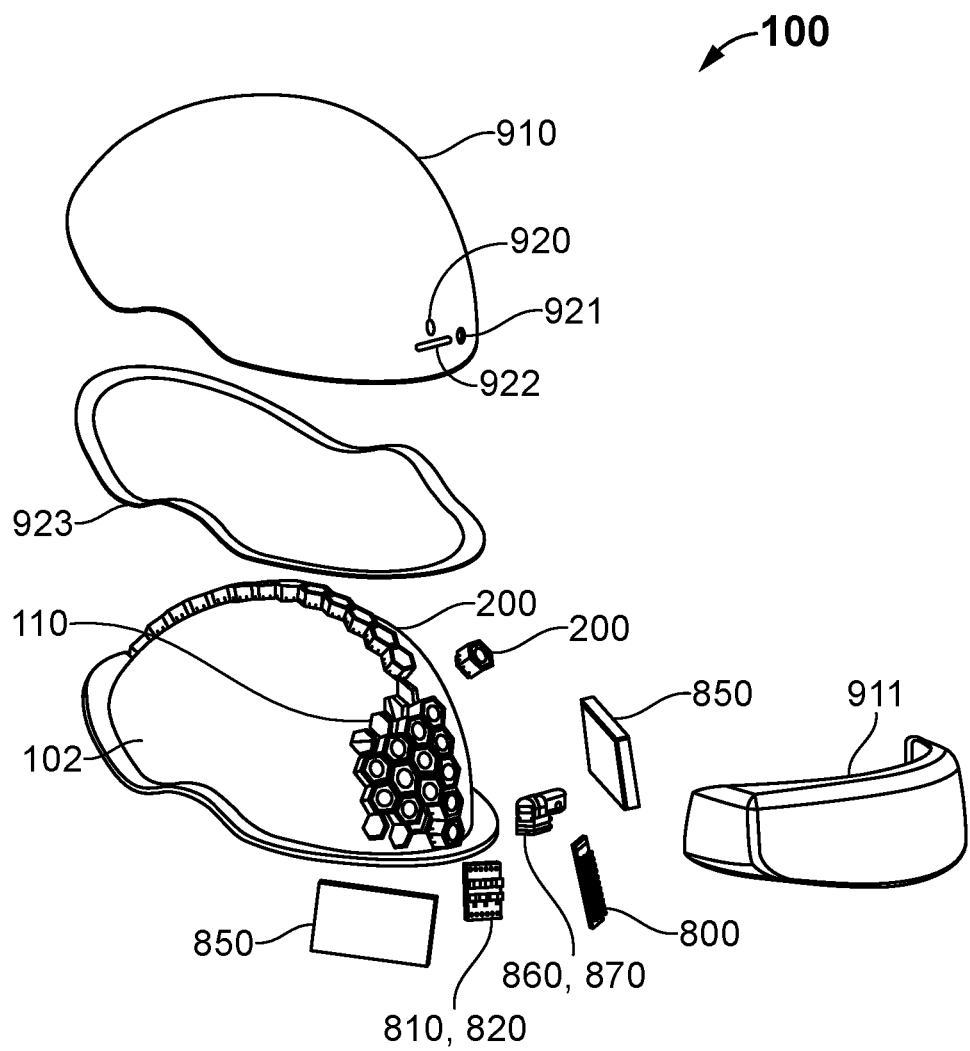
FIG. 10 illustrates system-level components of a light therapy device, according to an alternative embodiment of the present invention.

Referring to FIG. 10, the embodiment of FIGS. 9A-9C may comprise system-level components, including: a dome 102, a pneumatic shell 910, and a seal 923 disposed therebetween; one or more illumination assemblies 200; various electronic and mechanical components such as one or more LED boards 810, 820, one or more batteries 850, a master control board 800, and one or more pumps 860, 870; and a rear cover 911. Pneumatic shell 910 may include one or more pressure sensors 920, one or more pneumatic ports 921, and one or more light source drive circuit ports 922. Once assembled, components housed within the rear cover 911 may acuate pressurization through said one or more pneumatic ports 921, in the manner previously described.

Referring to FIG. 11, the embodiment described in FIG. 10 may further comprise one or more illumination assemblies 200 including an elastic actuator assembly 900, a biasing element 904, a cover plate 905, a light source 906a, first and second electrical contacts 906b, 906c, an optical assembly 208, first and second electrical terminals 906d, 906e, a carriage 907, and a seal 908. Elastic actuator assembly 900 may include top plate 901, a bottom plate 903, and an elastic layer 902 disposed therebetween. Carriage 907 may include: one or more carriage fasteners 907a, configured to couple to opening 110 of dome structure 102 wherein dome structure 102 may include depressions 111; one or more terminal receivers 907b, configured to receive terminal receivers 906d, 906e, and which may couple the same to an integrated circuit board (PCB) within the dome structure 102; first and second ends 907d, 907e, respectively; and one or more seal receivers 907c. Additionally, seal 908 may include one or more seal fasteners 908a, configured to couple to carriage 907 via seal receivers 907c. The variety of components comprising illumination assembly 200 may be assembled and made operational via snap-fit, gluing, spot-welding, and/or via other manufacturing technology and methods.

Referring now to FIGS. 12A-12C, an illumination assembly 200 according to the embodiment described with respect to FIG. 11 is shown in an assembled/operational configuration. Elastic layer 902 is shown in a planar configuration within carriage 907, in a condition corresponding to a first position 720 as provided diagrammatically in FIG. 9A or 9C. Importantly, the assembly/operational elastic actuator assembly 900 is characterized in that the design allows for a maximum amount of exposed surface area of the elastic layer 902 as confined by the geometry of the carriage so as to maximize the pressure exerted upon the same, corresponding to said second position 721. In an alternative embodiment, the aperture formed by top and bottom plates 901, 903, forms a diameter attenuated to the desired pressure seen on the surface of the elastic layer 902, which may be less than the maximum allowable diameter according to said geometric limitations. Elastic layer 902 may be made of an elastomeric material such as rubber, or any other appropriately elastic material subject to desirable elasticity characteristics subjected to high cycle-fatigue conditions.

In operation, infiltrated fluid 705 exerts a pressure on elastic layer 902 causing the same to deform thereby exerting a corresponding pressure on cover plate 905, which in turn urges linear translation of first and second electrical contacts 906b, 906c, light source 906a, and optical assembly 208. This action extends optical assembly 208 to second position 721 as shown in FIG. 9B and FIG. 12B. The biasing element 904 absorbs potential energy as pressure is applied, thereby providing a reactionary force to return illumination assembly 200 to the first position 720 as shown in FIGS. 9A, 9C, 12A and 12C. First and second electrical contacts 906b and 906c may be configured to slide along surface of first and second electrical terminals 906d, 906e, as shown in FIGS. 12B and 12C. Also as shown, first and second electrical terminals 906d, 906e extend outwardly along first end 907d of carriage 907, to electrically couple to a surrounding circuit. In an alternative embodiment, first and second electrical terminals 906d, 906e at a lower end, i.e., toward second end 907e of carriage 907 continue to run through carriage 907 and couple electrically to a circuit embedded within the dome 102. In this way, the electrical circuitry components of light therapy device 100 may be removed from the interstitial space 730. Regarding dome 102, an integrated circuit such as that shown in FIG. 14, may comprise an insulating substrate formed according to known methods, e.g., surface, silicon-on-insulator (SOI), and bulk machining. These configurations may apply to the embodiments shown with respect to FIG. 3, and/or the wiring extending through interstitial space 730 may be applied to the embodiments covered by FIGS. 11-12C. Similarly, the characteristics of light source 207, described above, may be employed here with respect to light source 906a.

Figure 14:
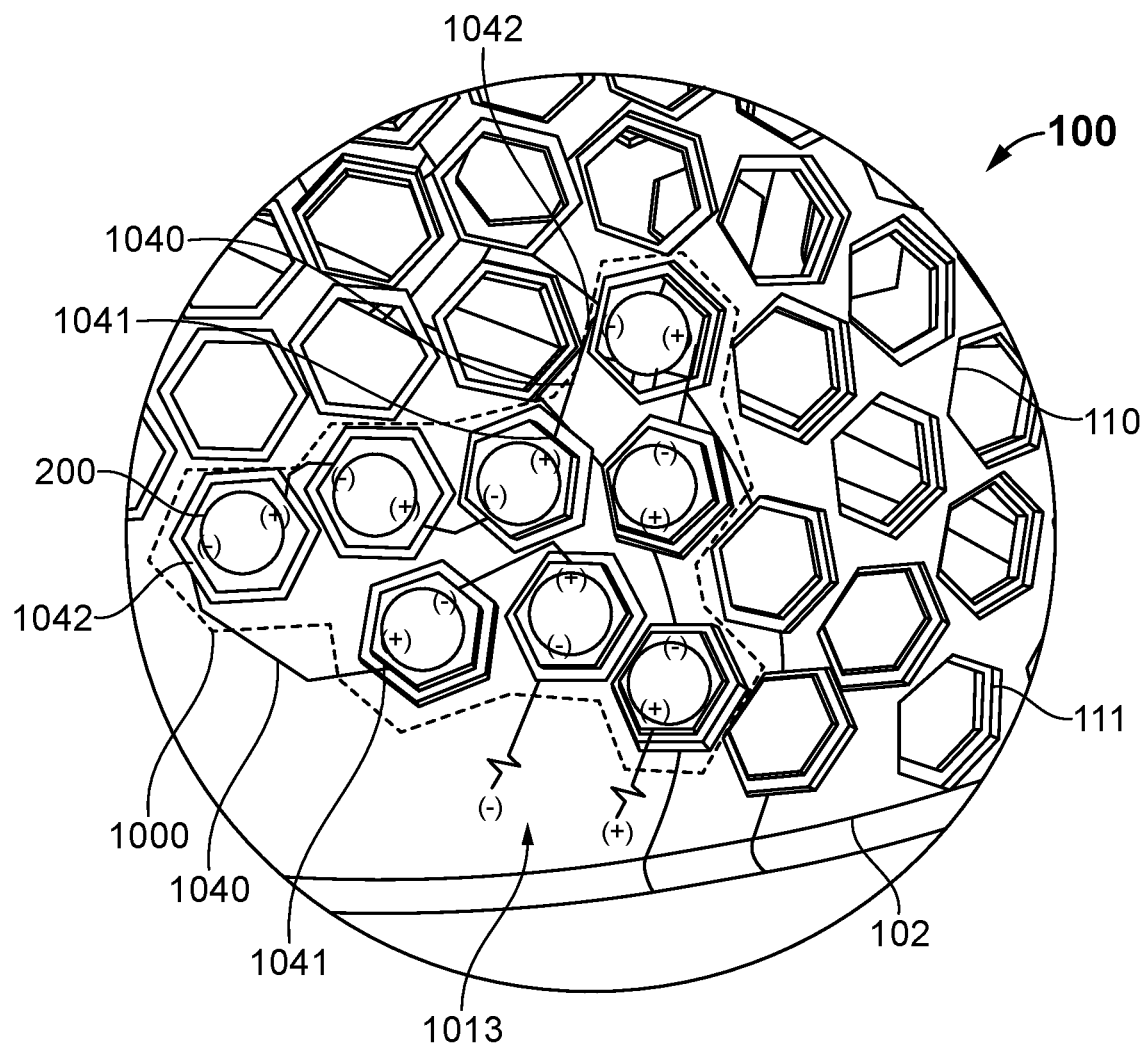
FIG. 14 is a schematic diagram view, taken along lines 14-14 of FIG. 1, illustrating an exemplary illumination zone of one or more light sources electrically controlled by the control system of the invention.

Referring now to FIGS. 13 and 14, an exemplary control schematic of light therapy device 100 is provided. As to FIG. 13, representative components may be disposed within or around the light therapy device 100, as appropriate, which may include a master control board 800, first and second LED boards 810, 820, a power switch 830, a charging port 840, one or more batteries 850, one or more pumps 860, 870, and a transceiver 880—electrically and/or communicatively coupled in the manner diagrammatically shown. Illumination assemblies 200 may be serial coupled to provide constant current through each light source 207, 906a. In an alternative embodiment, illumination assemblies 200 may be coupled in a parallel configuration. In one embodiment, one or more illumination assemblies 200 are grouped in about ten (10) cells 200 per zone, and arranged on the dome 102 for ease of assembly, e.g., to minimize electrical jogging across a given zone. However, any number of illumination assemblies may be grouped into a single zone, for example, to correspond to commonly-known patterns of alopecia, such that, e.g., illumination intensity may be attenuated by zone according to one or more applicable patterns.

An exemplary zone 1000 is illustrated in FIG. 14, which corresponds to the enlarged view called out in FIG. 1. Exemplary zone 1000 further corresponds to the thirteenth string 1013, illustrated in FIG. 13, extending to/from LED Board 1, 810. Again referring to FIG. 14, a conductive portion 1040 may be interlaid between adjacent and/or jogged openings 110, each conductive portion comprising a first end 1041 and a second end 1042. The exemplary zone 1000 terminates at either end, according to the positive (+) and negative (−) terminals indicated. Each conductive portion 1040 and terminal ends may be embedded in the dome 102 according to the methods previously described; or, the conductive portions 1040 may form wires that pass through interstitial space 730. Additionally, exemplary zone 1000 may generally describe any of the strings 1001-1021 illustrated in FIG. 13.

As shown in FIG. 13, control may be discretized into zones, for example, as strings 1001-1021. As previously mentioned, control implementation may be based upon known and available LED products which are capable of operating to produce light at two separate wavelength bands, i.e., at 668-684 nm and 813-846 nm, simultaneously. Such LEDs are considered for use herein. Similarly, with respect to the arrangement of light sources across the entire dome 102, any combination of useful operating conditions may be employed, including but not limited to: LEDs operating at one or more wavelength bands corresponding to a single string of LEDs wired and controllable together; LEDs operating at one or more wavelength bands corresponding to a known localized alopecia pattern; LEDs operating at one or more wavelength bands corresponding to a desired light output intensity at a localized area, distinguishable from LEDs operating at one or more wavelength bands corresponding to a separate, localized area; and LEDs operating at one or more wavelength bands at a localized area, distinguishable from LEDs operating at one or more wavelength bands corresponding to a separate, localized area.

Additionally, each string 1001-1021 may comprise a ground as indicated in FIG. 13, which may be a common ground tied to that of the one or more batteries 850. The transceiver 880 may communicate wirelessly or hard-wired to an external device, such as a smart phone 890. Transceiver 880 may update the light therapy protocol as controlled by master control board 800, so as to accommodate for desirable effects, such as software updates, and feedback on therapy protocol as the therapy progresses. The devices and methods described herein can optimize cell proliferation (i.e. growth of hair) with low doses over longer periods of time.

It is believed that LLLT/PBM creates a dose dependent effect so each dose builds on the previous treatment (and the Arndt-Schulz Law means that too much dose has suppressive effects). Therefore, the assemblies disclosed herein allow for a uniform treatment applied to that avoids the suppressive effects of over-treatment. In one example, it was found that 14-20 minutes applied every few days was sufficient to penetrate to the depth of the hair follicle within the skin.

The previous description of the disclosed embodiments is provided to enable any person skilled in the art to make or use the present invention. Various modifications to these embodiments will be readily apparent to those skilled in the art, and the generic principles defined herein can be applied to other embodiments without departing from the spirit or scope of the invention. For example, a wide variety of materials may be chosen for the various components of the embodiments. It is therefore desired that the present embodiments be considered in all respects as illustrative and not restrictive, reference being made to the appended claims as well as the foregoing descriptions to indicate the scope of the invention.

What is claimed is:

1. A device for positioning over and applying electromagnetic energy to a body organ, the device comprising:
   a dome forming a contoured shape, said dome including a plurality of dome openings, where an interior space of the contoured shape is adapted for placement over the body organ;
   a plurality of illumination assemblies each including an optical assembly having a proximal end optically coupled to a light source, a distal end configured to direct electromagnetic energy to the body organ, and a group of light guides therebetween, each of said illumination assemblies being coupled to said dome to allow said optical assembly to move freely through one of said dome openings; and
   an actuator configured to move each optical assembly of said plurality of optical assemblies, upon activation, from a first position to a respective second position corresponding to a conformal arrangement around a body organ, and upon deactivation, to move said plurality of optical assemblies back to said first position;
   wherein the device further comprises a biasing element for each illumination assembly of said plurality of illumination assemblies, said biasing element being coupled between said optical assembly and a carriage of said illumination assembly, said biasing element configured to move said plurality of optical assemblies back to said first position,
   and wherein the device further comprises a shell surrounding said dome and spaced apart from the same to form an interstitial space, and an interstitial reservoir disposed within said interstitial space, said interstitial reservoir configured to actuate said plurality of illumination assemblies by inflating the same, wherein upon deactivation, said interstitial reservoir deflates to allow said biasing element to move said plurality of optical assemblies back to said first position.

2. The device of claim 1 wherein said actuator is selected from the group consisting of: a biasing actuator, a hydraulic actuator, a pneumatic actuator, an electrical actuator, a thermal actuator, a magnetic actuator, and a soft actuator.

* * * * *